US00PP08180P

United States Patent [19]

VandenBerg

[11] Patent Number: Plant 8,180

[45] Date of Patent: Mar. 16, 1993

[54] CHRYSANTHEMUM PLANT NAMED CORRIDA

[75] Inventor: Cornelis P. VandenBerg, Salinas, Calif.

[73] Assignee: Yoder Brothers, Inc., Barberton, Ohio

[21] Appl. No.: 745,700

[22] Filed: Aug. 16, 1991

[51] Int. Cl.[5] ..... A01H 5/00

[52] U.S. Cl. ..... Plt./82.4

[58] Field of Search ..... Plt./74.1, 82.4

*Primary Examiner*—Howard J. Locker

*Attorney, Agent, or Firm*—Foley & Lardner

[57] ABSTRACT

A Chrysanthemum plant named Corrida particularly characterized by its flat capitulum form; spooned anemone capitulum type; light purple ray floret color; diameter across face of capitulum of 76 to 83 mm when fully opened, when grown as a single stem spray cut mum; flowering response in Salinas under normal temperatures is 49 to 55 days after start of short days; flowering response in Bogota, Colombia under temperatures of minimum 6.3 degrees Celsius night and maximum 29 degrees Celsius day is 64 to 70 days; plant height is 76 to 86 cm when grown in Salinas with 14 long days prior to start of short days; height is 102 to 117 cm when grown in Bogota with 21 long days prior to start of short days; peduncle length of the first lateral at flowering after removing the apical bud without growth regulator applications is 5 to 8 cm when grown in Salinas and in Bogota; peduncle length of the fourth lateral at flowering is 10 to 18 cm when grown in Salinas, and 10 to 13 cm when grown in Bogota; and excellent tolerance to low night temperatures for bud initiation and flower development.

3 Drawing Sheets

The present invention comprises a new and distinct cultivar of Chrysanthemum, botanically known as *Dendranthema grandiflora,* and referred to by the cultivar name Corrida.

Corrida, identified as 3447 (86-910010), was originated from a cross made by Cornelis P. VandenBerg in a controlled breeding program in Salinas, Calif., in 1986.

The female parent of Corrida was an unnamed seedling, identified as 1443 (83-754009), and described as a flat spooned anemone cut spray mum with a light pink ray floret color; a flowering response in Salinas, Calif. of 53 to 62 days; a plant height of 69 to 84 cm when grown with 14 to 15 long days prior to start of short days; and a peduncle length of the first lateral of 8 to 10 cm and of the fourth lateral of 13 to 18 cm, when grown in Salinas, Calif. The female parent was tested once in Bogota, Colombia in 1985, and was discarded from the Bogota program because the plants rosetted and remained vegetative, with no flowering occurring. The female parent was completely discarded from all programs in June 1988.

The male parent of Corrida was an unnamed seedling, identified as 5549 (84-112016), and described as a flat daisy spray cut mum with a streaked pink and white ray floret color; a flowering response to short days of 51 to 61 days in Salinas, Calif., and of 64 to 66 days in Bogota, Colombia; a plant height when grown in Salinas with 6 to 7 long days prior to start of short days of 81 to 99 cm; a plant height when grown in Bogota with 7 long days prior to start of short days of 114 to 117 cm; a peduncle length of 10 to 13 cm of the first lateral and 15 to 18 cm of the fourth lateral when grown in Salinas; and a peduncle length of the first lateral of 10 cm and of 15 to 18 cm of the forth lateral when grown in Bogota. The male parent was discarded from the Colombian program in October 1987 because of poor performance, and was discarded completely from all programs in January 1988.

Corrida was discovered and selected as one flowering plant within the progeny of the stated cross by Cornelis P. VandenBerg in May 1987, in a controlled environment in Salinas, Calif.

The first act of asexual reproduction of Corrida was accomplished when vegetative cuttings were taken from the initial selectiton in July 1987 in a controlled environment in Salinas, Calif., by technicians working under supervision of Cornelis P. VandenBerg.

Horticultural examination of controlled flowerings of successive plantings has shown that the unique combination of characteristics as herein disclosed for Corrida are firmly fixed and are retained through successive generations of asexual reproduction.

Corrida has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif., and in Bogota, Colombia, under greenhouse conditions which approximate those generally used in commerical greenhouse practice. The low temperature tolerance was determined in repeated flowerings in Bogota, Colombia, with an average minimum low night temperature inside the greenhouse during our trials ranging from 6.3 to 10.0 degrees Celsius.

The following traits have been repeatedly observed and are determined to be basic characteristics of Corrida, which, in combination, distinguish this Chrysanthemum as a new and distinct cultivar:

1. Flat capitulum form.
2. Spooned anemone capitulum type.
3. Light purple ray floret color.
4. Diameter across face of capitulum of 76 to 83 mm when fully opened, when grown as a single stem spray cut mum.

5. Flowering response in Salinas under normal temperatures is 49 to 55 days after start of short days. Flowering response in Bogota, Colombia under temperatures of minimum 6.3 degrees Celsium night and maximum 29 degrees Celsius day is 64 to 70 days.
6. Plant height is 76 to 86 cm when grown in Salinas with 14 long days prior to start of short days; height is 102 to 117 cm when grown in Bogota with 21 long days prior to start of short days.
7. Peduncle length of the first lateral at flowering after removing the apical bud and without growth regulator applications is 5 to 8 cm when grown in Salinas and in Bogota. Peduncle length of the fourth lateral at flowering is 10 to 18 cm when grown in Salinas, and 10 to 13 cm when grown in Bogota.
8. Excellent tolerance to low night temperatures for bud initiation and flower development.

The accompanying photographic drawings show typical inflorescence and leaf characteristics of Corrida, with the colors being as nearly true as possible with illustrations of this type.

Sheet 1 is a color photograph of Corrida grown as a single stem spray cut mum.

Sheet 2 is a black and white photograph of three views of the inflorescence of Corrida.

Sheet 3 is a black and white photograph showing the upper and under sides of the leaves of Corrida at 3 stages of development (mature, intermediate and immature).

In sheets 2 and 3 a measuring tape in centimeters has been added.

The combination of capitulum form and type and ray floret color is not represented in any cultivar known to the inventor, and no comparison can therefore be made.

When compared with both parents, the most obvious difference between Corrida and the parents is the performance in Bogota, Colombia. The female parent did not flower at all in Bogota, and was discarded after one flowering trial. The male parent was discarded because of poor performance. Corrida has shown an excellent performance under the Bogota conditions, with excellent tolerance to low night temperatures.

In the following description color references are made to The Royal Horticultural Society Colour Chart. The color values were determined on plant material grown as a single stem spray mum in Salinas, Calif. on Sep. 12, 1990.

Classification:

*Botanical.*—*Dendranthema grandiflora* cv. Corrida.

*Commercial.*—Spooned anemone spray cut mum.

INFLORESCENCE

A. Capitulum:

*Form.*—Flat.

*Type.*—Spooned anemone.

*Diameter across face.*—76 to 83 mm when fully opened.

B. Corolla of ray florets:

*Color (general tonality from a distance of three meters).*—Light purple.

*Color (upper surface).*—75C to 75D.

*Color (under surface).*—75C to 75D.

*Shape.*—Base tubular, apex flattened and spoon-like, with varying spoon length (see photograph).

C. Corolla of disc florets:

*Color (mature).*—12B.

*Color (immature).*—145B.

D. Reproductive organs:

*Androecium.*—Present on disc florets only; no pollen.

*Gynoecium.*—Present on both ray and disc florets.

PLANT

A. General appearance:

*Height.*—76 to 86 cm when grown in Salinas with 14 long days prior to start of short days, and 102 to 117 cm when grown in Bogota with 21 long days prior to start of short days.

B. Foliage:

*Color (upper surface).*—147A.

*Color (under surface).*—147B.

*Shape.*—See photograph.

I claim:

1. A new and distinct Chrysanthemum plant named Corrida, as described and illustrated.

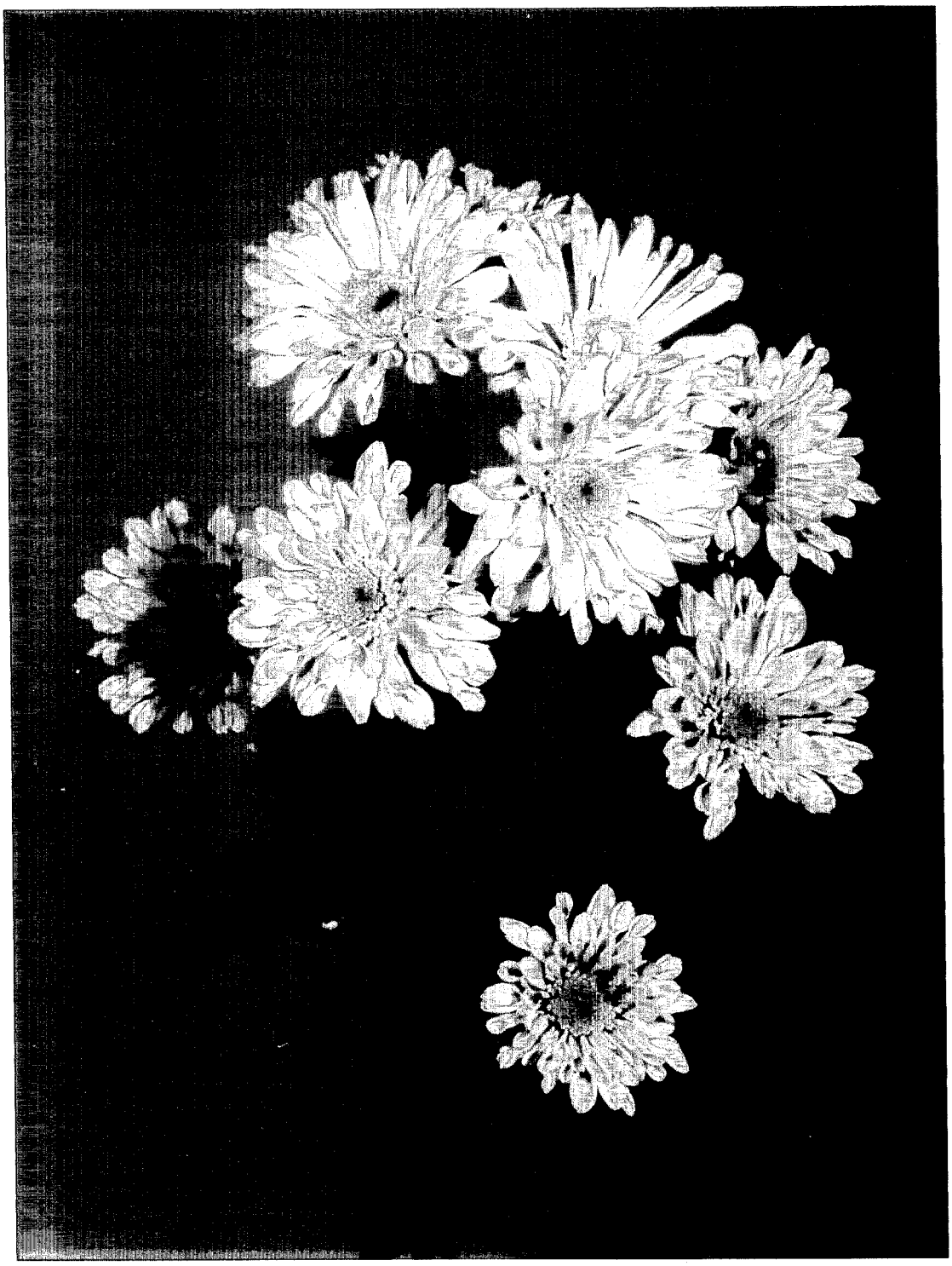

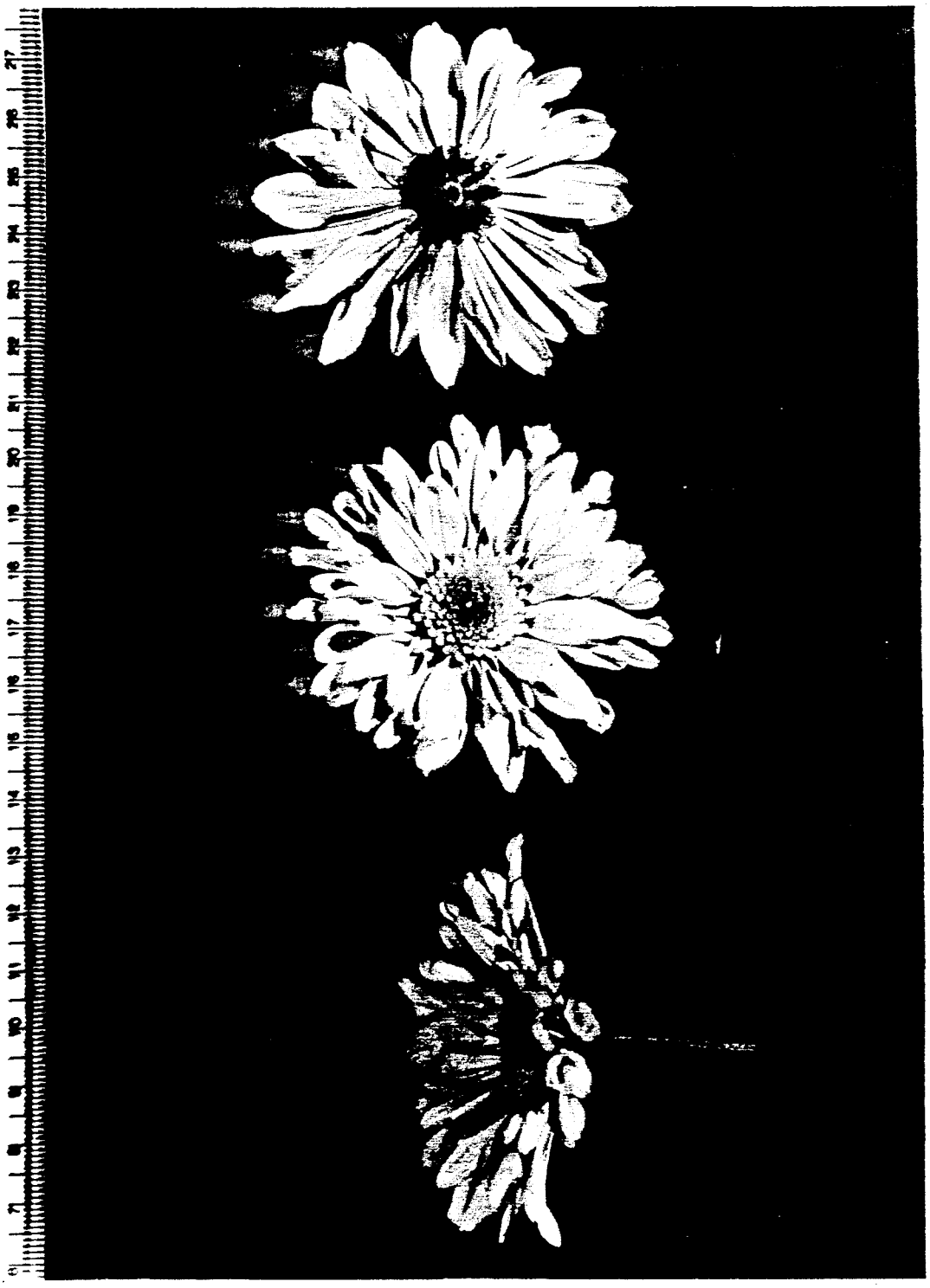

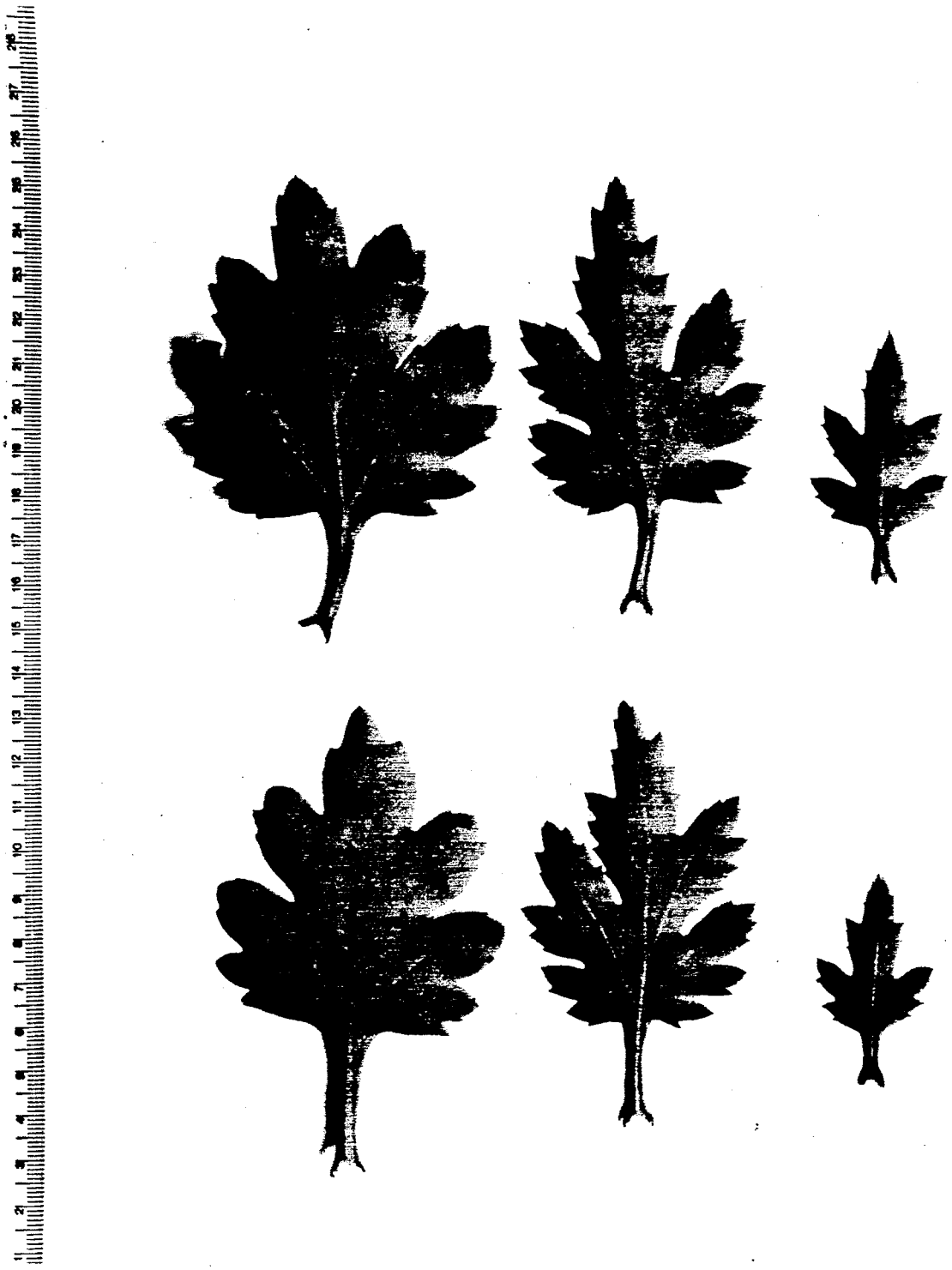

* * * * *